United States Patent [19]

Schneider et al.

[11] Patent Number: 4,882,269

[45] Date of Patent: Nov. 21, 1989

[54] AMPLIFIED HYBRIDIZATION ASSAY

[75] Inventors: Robert J. Schneider, New York, N.Y.; Thomas E. Shenk, Princeton, N.J.

[73] Assignee: Princeton University, Princeton, N.J.

[21] Appl. No.: 940,712

[22] Filed: Dec. 11, 1986

Related U.S. Application Data

[63] Continuation-in-part of Ser. No. 808,695, Dec. 13, 1985 now abandoned.

[51] Int. Cl.$^4$ ............................ C12Q 1/68; C12Q 1/42; C07H 21/00

[52] U.S. Cl. ............................................ 435/6; 435/18; 435/21; 435/803; 435/810; 935/78; 536/27; 436/800; 436/805; 436/808

[58] Field of Search ............................ 435/6, 18, 21, 803, 435/810; 935/78; 536/27; 436/501, 800, 805, 808

[56] References Cited

U.S. PATENT DOCUMENTS

| | | |
|---|---|---|
| 4,358,535 | 11/1986 | Falkow et al. . |
| 4,486,539 | 12/1984 | Ranki et al. . |
| 4,563,419 | 1/1986 | Ranki et al. . |
| 4,581,333 | 4/1986 | Kovrilsky et al. . |
| 4,617,261 | 10/1986 | Sheldon, III et al. . |
| 4,626,501 | 12/1986 | Landes . |
| 4,670,380 | 6/1987 | Dattagupta . |
| 4,699,876 | 10/1987 | Libeskind . |
| 4,716,106 | 12/1987 | Chiswell . |
| 4,751,177 | 6/1988 | Stabinsky . |
| 4,755,458 | 7/1988 | Rabbani et al. . |

FOREIGN PATENT DOCUMENTS

| | | |
|---|---|---|
| 0128018 | 12/1984 | European Pat. Off. . |
| 0128332 | 12/1984 | European Pat. Off. . |
| 0130523 | 1/1985 | European Pat. Off. . |
| 0138357 | 4/1985 | European Pat. Off. . |
| 0144914 | 6/1985 | European Pat. Off. . |
| 0153873 | 9/1985 | European Pat. Off. . |
| 0204510 | 12/1986 | European Pat. Off. . |
| 8403520 | 9/1984 | PCT Int'l Appl. . |
| 8502628 | 6/1985 | PCT Int'l Appl. . |

OTHER PUBLICATIONS

Dunn, A. R. et al., In Methods in Enzymology, 65, Part I (Grossman, L. et al., ed.), Academic Press, NY, 1980, pp. 468–478.
Rigby et al., 1977, J. Mol. Biol. 113:237–251.
Langer et al., 1981, PNAS, 78:6633–6637.
Melton et al., 1984, Nucl. Acids Res. 12:7035–7056.
Forster et al., 1985, Nucleic Acids Res. 13(3):745–761.
Dunn et al., 1977, Cell 12:23–36.
Ruyechen & Wetmur, 1975, Biochem. 14:5529–5534.
Sancar & Rupp, 1979, BBRC 90:123–129.
Schneider & Wetmur, 1982, Biochemistry 21:608–615.
Kochetkov et al., 1971, Tetahedran Lett., 1993–1996.
Barrio et al., 1972, BBRC, 46:597–604.
Lee & Wetmur, 1973, BBRC, 50:879–885.
Alwine et al., 1979, Methods Enz. 68:220–2420.
Thomas, 1980, Proc. Natl. Acad. Sci: 77(9):5201–5205.
Woodhead and Malcolm, Apr., 1984, Biochem. Soc. Trans 12:279–280.
Ranki et al., 1983, Gene 21:77–85.
Molden et al., 1985, Clin. Physiol. Biochem. 3:174–183.
Syvanen et al., 1985, Nuc. Acid. Res. 13(8):2789–2802.
Collins and Hunsaker, 1985, Anal. Biochem. 151:281–224.

*Primary Examiner*—Johnnie R. Brown
*Assistant Examiner*—Jeremy M. Jay

[57] ABSTRACT

An amplified hybridization assay is described in which a family of signal-generating secondary probes bind to a primary probe that hybridizes to the target sequence of interest. Thus, an enormously amplified signal is generated by the hybridization event. The assay can be used for a variety of laboratory and clinical purposes and is automatable.

62 Claims, 5 Drawing Sheets

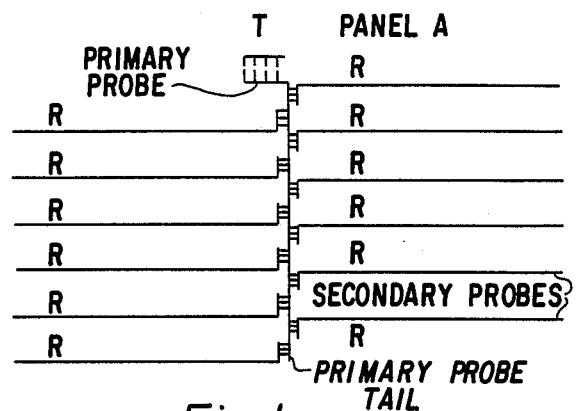
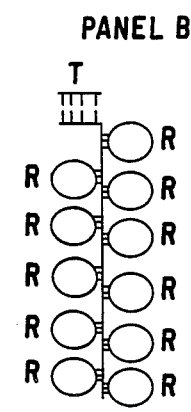
Fig.1a
Fig.1b
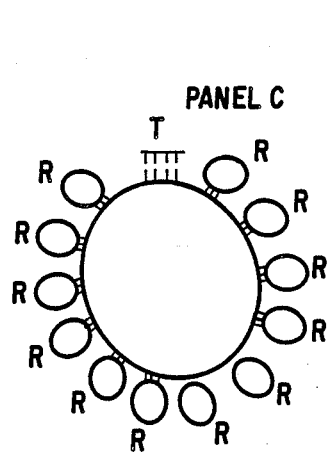
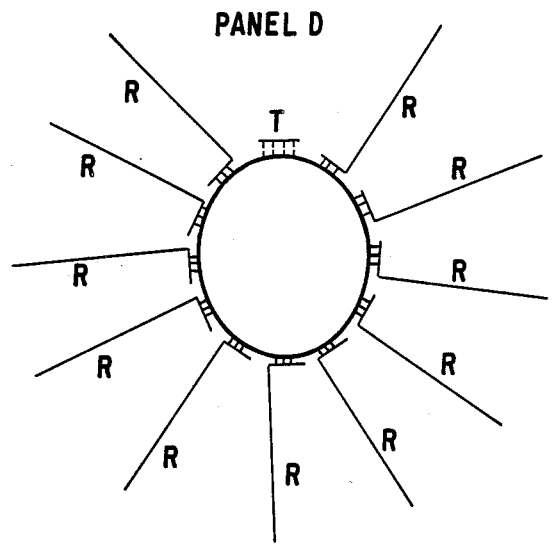
Fig.1c
Fig.1d

Tn5 SECONDARY PROBE DNAs

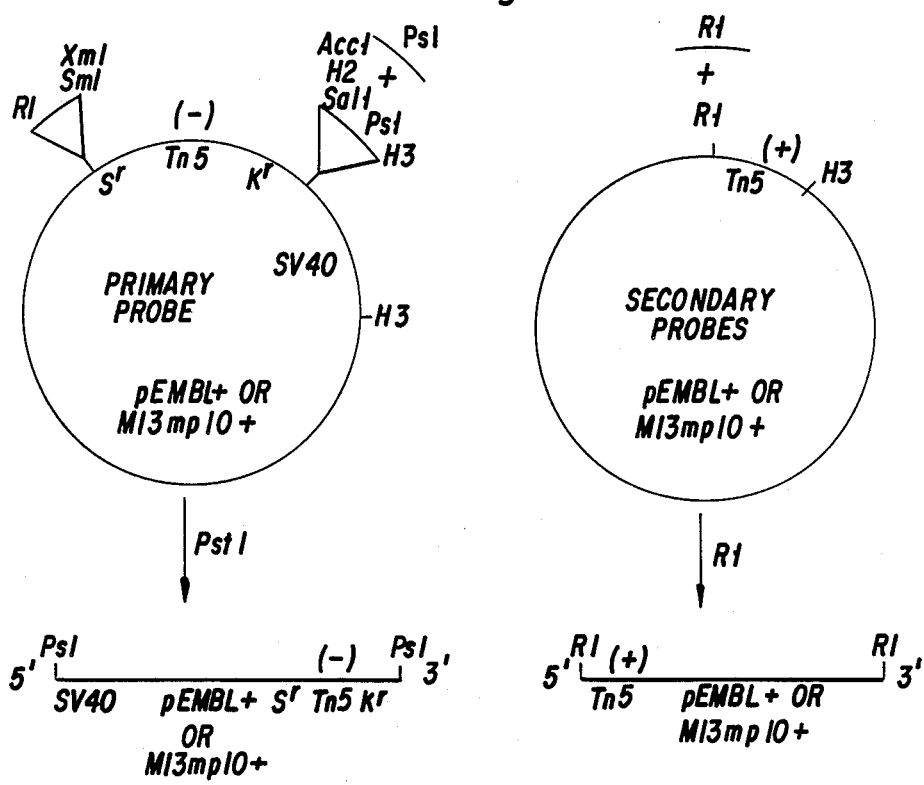
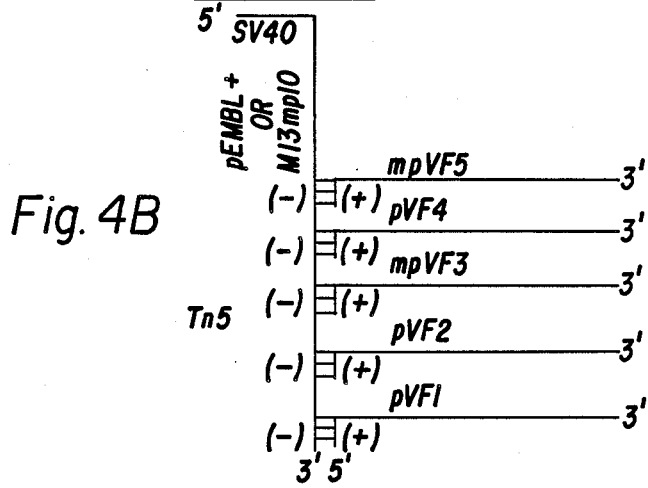

AMPLIFIED HYBRIDIZATION ASSAY

The present application is a continuation-in-part of copending application Ser. No. 808,695, filed Dec. 13, 1985, which is incorporated by reference herein in its entirety.

TABLE OF CONTENTS

1. Introduction
2. Background of the Invention
   2.1. Hybridization Assays
   2.2. Modification to Nucleic Acids
      2.2.1. Proteins That Bind Nucleic Acids
      2.2.2. Chemical Modifications of Nucleic Acids
3. Summary of the Invention
3. Summary of the Invention
   3.1. Definitions
4. Brief Description of the Figures
5. Description of the Invention
   5.1. Primary Probes
   5.2. Secondary Probes
   5.3. Reporter Groups
      5.3.1. Conversion of Secondary Probes to Reporter Groups
   5.4. The Hybridization Assays
   5.5. Automation of Hybridization Assay
6. Example: Construction of Primary and Secondary Probes for use in Amplified Hybridization Assays
   6.1. Materials and Methods
   6.2. Construction of Primary Probe Cassettes
   6.3. Construction of Secondary Probes
7. Example: Detection of Target DNA Using an Amplified Radiolabeled Hybridization Assay
   7.1. Materials and Methods
      7.1.1. Insertion of the Target Sequence into the Primary Probe Cassette
      7.1.2. Radioactive Labeling of Secondary Probes
      7.1.3. Hybridization Procedure
   7.2. Detection of Target DNAs
8. Example: Ultrastructural Analysis of the Hybridization Complexes
9. Example: Demonstration of Hybridization Complexes Using Non-Radioactive Labels
   9.1. Materials and Methods: Photobiotinylation and Color Development
   9.2. Detection of Hybridization Complexes
   9.3. Amplification of Signal

1. INTRODUCTION

The present invention concerns hybridization assays that employ detection systems which provide for enormous amplification of the signal generated by the reporter groups used in the assay. Primary probes which hybridize to the target sequence of interest are described. An amplified signal is achieved by the binding of a family of secondary signal-generating probes to multiple sites on the primary probe.

The hybridization and detection assays described herein can be used as a kit and can also be fully automated for the detection of nucleic acid sequences in the research and clinical laboratory, as well as in food, agricultural and veterinary sciences. It is a very powerful diagnostic device for the detection of pathogenic organisms (bacteria, viruses, fungi, yeast, protozoa) in human and veterinary medicine, and for the detection of cancerous cells and genetic defects in chromosomes.

2. BACKGROUND OF THE INVENTION

Nucleic acid hybridization assays have the potential to become powerful tools in the diagnosis of medical and veterinary disorders caused by pathogenic organisms, cancerous cells and genetic defects in chromosomes. However, a number of problems exist with the current technology which makes its application to diagnostics impractical. The assay must be extremely sensitive, reproducible, require few technical manipulations and thus be suitable for kits and automation.

2.1. HYBRIDIZATION ASSAYS

The most common method for the detection of specific nucleic acid sequences (DNA or RNA) is achieved by hybridization of radioactive probes and autoradiography. Traditionally, radioactive probes have been produced by nick-translation (Rigby et al., 1977, J. Mol. Biol. 113, 237–251), and more recently by SP6 transcription (Melton et al., 1984, Nucl. Acids. Reg. 12, 1735–7056). These methods generate radioactive probes of high specific activity which are capable of detecting small concentrations of DNA or RNA sequences. However, there are several disadvantages to these methods. First, the production of probes requires the use of radioactive isotopes which have short half-lives necessitating a continuous production of fresh probes. Second, the labeling procedure requires the use of enzymes which are expensive and require reaction conditions which must be very carefully calibrated. Third, radioactive isotopes are biologically dangerous to use. In fact, their use requires proper licensing, and their disposal is becoming increasingly expensive, difficult and hazardous.

A non-radioactive hybridization probe has been developed which utilizes biotinylated nucleotide analogues which are synthesized into probes using procedures described previously for the production of radioactive probes (Langer et al., 1981; Proc. Natl. Acad. Sci. USA 78, 6633–6637). Hybridization of the probes to the target sequence is detected by the interaction of biotin with avidin-conjugated enzymes, fluorescent compounds, or enzyme linked immunodetection systems. Although the use of radioactivity is eliminated, several problems are associated with the biotin-avidin technique. One problem is sensitivity; for the most part, biotinylated probes are not as sensitive as radioactive probes. Another problem encountered is that the alteration of the nucleotides interferes with hybridization of the probe to its target.

Hybridization assays using various signal generating systems have been developed. For example, a non-radioactive hybridization assay system which utilizes the chemical modification of nucleic acids that makes them more immunogenic has been reported (Herzberg, EP O 128 018 A2). The signal is generated by reporter groups containing antibodies which recognize the altered nucleic acid. Radioactively labeled or biotinylated *Escherichia coli* single strand DNA binding protein (SSB) crosslinked to filamentous phage M13 ssDNA containing a nuclei acid sequence complementary to the target gene has recently been used as a probe in a hybridization assay system (Synaven et al., 1985, Nucl. Acids. Res. 13, 2789–2802). In another hybridization system the adenine and cytosine nucleic acid bases of the probe are bonded to reporter groups by chemical modification (Landes, EP O 138 357 A2 and U.S. Pat. No. 4,626,501).

The hybridization assays thus far described require the preparation of labeled probes each of which hybridizes to a different target sequence. In order to reduce the number of labeled probes that must be prepared, a hybridization assay has been developed which utilizes a "bridging" polynucleotide between the target nucleic acid and a general signaling polynucleotide. The bridging polynucleotide consists of a single-stranded filamentous bacteriophage which contains nucleic acid sequences complementary to the target gene. The general signaling polynucleotide is a segment of single strand phage DNA which is complementary to the bridging polynucleotide (Pergolizzi et al., EP O 128 332 A1; Chiswell, EPO 153 873 A2).

Another problem associated with hybridization assays involves the removal of labeled probes that do not hybridize to the target sequence from the hybridization reaction because the presence of non-hybridized probes in the hybridization reaction leads to a false positive result. A hybridization assay has been described which claims to obviate the requirement for separation of non-hybridized probes (Albarella et al., EPO 144 914 A2). This system requires th cohybridization of two components which when associated generate a signal. Another hybridization assay has been described which utilizes photochemically reactive intercalating agents for the covalent attachment of nucleic acids to solid supports (Dattagupta and Crothers EP O 130 523 A2). The immobilized target nucleic acids are capable of hybridization. Another immobilized hybridization assay system involves first hybridizing and then forming covalent bonds between the probe and target sequence (Yabusaki, et al., WO85/02628). Immobilized sandwich hybridization techniques which require two distinct single stranded nucleotide probes have also been reported (Dunn et al., 1977, Cell 12: 23–36; Ranki et al., U.S. Pat. No. 4,563,419).

2.2. MODIFICATIONS TO NUCLEIC ACIDS

Modifications of nucleic acids have been performed for a variety of reasons. These include motivations as esoteric to the present invention as studies on the composition and/or structure of polynucleotides, as well as investigations into methods for coupling reagents and substrates to nucleic acid molecules. The alterations discussed below are grouped into two categories: (1) association of proteins with nucleic acids, and (2) chemical modification of nucleic acids.

2.2.1. PROTEINS THAT BIND NUCLEIC ACIDS

Proteins capable of binding to nucleic acids (RNA or DNA) include: (a) ssDNA binding proteins (e.g. E. coli SSB, bacteriophage T4 gene 32 protein, fd phage SSB), (b) dsDNA binding proteins (e.g. histones, polymerases), (c) ssRNA binding proteins (e.g. mRNP proteins), (d) dsRNA binding proteins (e.g. eukaryotic translation initiation factors).

E. coli SSB is particularly interesting for several reasons. SSB binds ssDNA independent of base composition, apparently by interacting with the phosphate backbone (Ruyechen and Wetmur, 1975, Biochem. 14: 5529-5534). The SSB gene has been cloned (Sancar and Rupp, 1979, BBRC 90, 123-129), permitting the protein to be purified in large quantities. SSB binds to ssDNA cooperatively, and therefore forms contiguous chains of protein. The protein is extraordinarily stable, and a scheme was developed for its purification in large quantities based upon its ability to withstand denaturation (Schneider and Wetmur, 1982, Biochemistry 21, 608-615). It was also demonstrated that the ssDNA molecules complexed to SSB are immune to degradation by nucleases.

2.2.2. CHEMICAL MODIFICATIONS OF NUCLEIC ACIDS

Many methods have been described, and are well known, for the covalent association of protein molecules with nucleic acids. These include, but are not limited to, crosslinking with glutaraldehyde, formaldehyde, glyoxal, carbodiimide, ultraviolet light, and oxidation/reduction systems.

The attachment of saccharides to nucleic acids has been described by a variety of research groups. The technique requires chemical activation of the nucleic acid and saccharides. Nucleic acid molecules have also been modified for the covalent attachment to cellulose paper by diazo coupling reactions (Alwine et al., 1979, Methods Enz. 68, 220-242). This technique has also been used to attach sugar and biotin moieties to nucleic acids.

Alkylating agents have been used to derivatize nucleic acid molecules. Chloroacetaldehyde is one example. The reaction of chloroacetaldehyde with adenine and cytosine nucleosides have been known since 1971 (Kochetkov et al., 1971, Tetrahedron Lett., 1993-1996). Chloroacetaldehyde reacts almost quantitatively with adenine and cytosine at slightly acidic conditions (pH 3.5 to 4.5) to produce a highly fluorescent 1, $N^6$-ethenoadenosine (etheno-A) derivative, and a less fluorescent 3,$N^4$-ethenocytidine (etheno-C) derivative (Barrio et al., 1972, BBRC 46, 597-604). No reaction occurs with uridine, thymidine, guanosine or inosine. Formation of ethanoderivatives with single-strand polyribonucleotides and polydeoxyribonucleotides does not result in any detectable chain scission. Fluorescence excitation is maximally achieved at 300 nm, with a corresponding fluorescence emission maximum at 410 nm for etheno-A and 347 nm for etheno-C. Chloroacetaldehyde has been used to modify accessible (i.e. non base-paired) nucleotides in RNA molecules (Barrio et al., 1972 BBRC 46, 597–604). Modification of polynucleotides with chloracetaldehyde inhibits their ability to participate in basepair formation (Lee and Wetmur, 1973, BBRC 50: 879-885). Another alkylating method for labeling nucleic acid involves intercalating the alkylating moiety of a labeling reagent into a partially double-stranded nucleic acid (Sheldon, U.S. Pat. No. 4,617,261).

3. SUMMARY OF THE INVENTION

The present invention is directed to a hybridization assay that generates an enormously amplified signal upon hybridization to the target sequence of interest. Accordingly, a primary probe is provided, a small segment of which hybridizes to the target DNA of interest. A family of signal-generating secondary probes that hybridize to different segments of the primary probe provide for an enormous amplification of the signal generated by the hybridization event. Depending upon the configuration of the assay components, the hybridization event may occur between mobile species or between combinations of fixed and mobile species. The invention is directed to the hybridization assay, the probes, signal-generation and methods of use.

The detection of the primary hybridization event in hybridization assays previously described have generally not been amplified by secondary events. In these systems, the magnitude of amplification is determined by the incorporation of reporter groups into the primary probe, and thus the signal to target ratio is severely restricted. The present invention discloses assays which provide for enormous amplification of the signal to target ratio by means of many secondary probe hybridization events directed to the primary probe, by means of attaching reporter groups to the secondary probes or modifying the secondary probes to become reporter groups, and by means for detecting these signals.

3.1. DEFINITIONS

The following terms, whether used in the plural or singular will have the meanings indicated:

The "primary probe" comprises a polynucleotide sequence which is complementary to the target sequence of interest attached to a "tail" that does not bind to the target sequence and is available for binding to other substances. The "tail" of the primary probe may comprise any of a number of polymers, including but not limited to single and double-stranded polynucleotides, and other natural or synthetic polymers such as cellulose, nylon, rayon, and the like. The primary probe may comprise linear or circular molecules.

The "secondary probes" comprise a family of signal-generating probes, each of which contains a segment capable of binding to a portion of the tail of the primary probe attached to a "signal-generating component". The composition of the secondary probes is dependent upon the composition of the tail of the primary probe; for example, where the tail of the primary probe is a single-stranded polynucleotide, the secondary probes can comprise a family of polynucleotides each of which contains a single-stranded portion that hybridizes to a segment of the primary probe tail. Other compositions are defined herein. The signal-generating component of the secondary probes may be conferred on the secondary probe by the attachment of reporter groups or by modification of the secondary probe so that the probe itself generates a detectable signal. The secondary probes may comprise linear or circular molecules.

The "reporter groups" are defined as any of a large variety of compounds which themselves generate a detectable signal or which generate a detectable signal after interaction with other compounds. These include the secondary probes which themselves can generate a detectable signal.

The "primary probe cassette" comprises a nucleotide vector containing (a) a multiple-cloning site into which any target nucleotide sequence can be inserted, and (b) additional nucleotide sequences to which the family of secondary probes can hybridize. In practice, a polynucleotide primary probe may be constructed using the primary probe cassette by inserting and cloning the target sequence into the multiple cloning site and purifying the single stranded form of the resulting recombinant nucleotide vector.

4. BRIEF DESCRIPTION OF THE FIGURES

Figures are not drawn to scale.

FIG. 1 is a representation of the mechanism of the present hybridization assay for the detection of target nucleic acid sequences. "T" represents the target nucleic acid sequence. "R" signifies any of a large variety of reporter groups attached to the secondary probes either directly or indirectly. Primary and secondary hybridization probes are indicated. Panel A depicts the hybridization complex formed when the primary and secondary probes are both linear molecules; this results in the formation of "Christmas tree" structures. Panel B depicts a variant of the hybridization complex resulting from an assay in which the primary probe is linear and the secondary probe is circular. Panel C represents the hybridization complex formed when both the primary and secondary probes are circular. Panel D represents the hybridization complex formed when the primary probe is circular and the secondary probe is linear.

FIG. 4 represents the use of the primary probes containing SV40 DNA and Tn5(−) sequences in conjunction with a family of secondary probes containing Tn5(+) sequences for the detection of SV40 target DNA. Panel A diagrammatically represents the linearization of the primary and secondary probes. Panel B diagrammatically represents the hybridization complexes which are formed when using the linearized probes of panel A.

Figure 5:
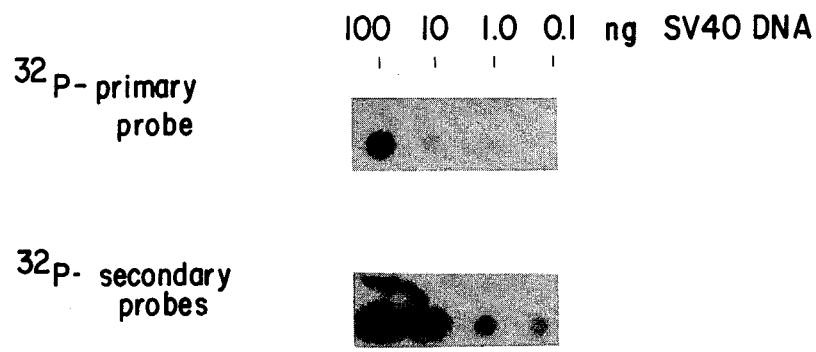

FIG. 5 demonstrates the amplified detection of target SV40 DNA using the method of the invention in a dot-blot format. In pane A, different amounts of target SV40 DNA were detected using a labeled $^{32}$P-primary probe as a control. In panel B, different amounts of target SV40 DNA were detected using the unlabeled primary probe and the family of labeled $^{32}$P-secondary probes in accordance with the method of the invention.

Figure 6:
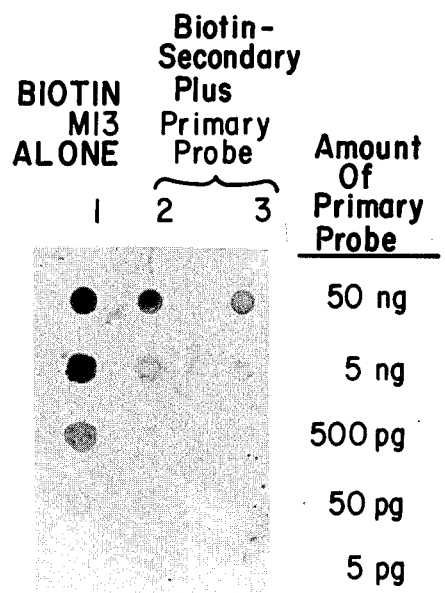

FIG. 6 demonstrates the amplified signal which can be generated using a primary probe in conjunction with its family of secondary probes labeled with a non-radioactive reporter group in a dot-blot format. In lanes 2 and 3, photobiotinylated secondary probes were hybridized to decreasing quantities of the primary probe cassette and hybridization was detected using an avidin-linked alkaline phosphatase colorimetric reaction. Lane 1 contains decreasing amounts of control biotinylated M13 ssDNA.

5. DESCRIPTION OF THE INVENTION

A hybridization assay is described for the detection and quantitation of specific nucleic acid sequences, and in particular, those corresponding to genes (DNA) and gene products (RNA). The assay system comprises a primary hybridization probe, a portion of which contains single strand nucleic acid sequences complementary to a target gene, and therefore hybridizes to it; the remainder of the primary probe cannot hybridize to the target sequence and is referred to as the tail. A family of secondary hybridization probes are provided, each of which contains a signal generating component attached to a segment which can bind to a portion of the tail of the primary probe. The secondary hybridization probes have been prepared in such a way that a large number are able to interact with each primary probe therefore, a large number of secondary probes bind to each primary probe which recognizes the target sequence. This results in an enormous amplification of the initial recognition event.

The primary and secondary probes may be linear or circular moieties that are used in any combination (see FIG. 1). For example, when both the primary and secondary probes are linear molecules the hybridization complex formed will have a "Christmas-tree" structure as shown in FIG. 1A. The hybridization complex that results from the use of circular primary and secondary probes are shown in FIG. 1C. The hybridization complexes that result from a mixture of linear and circular probes are shown in FIGS. 1B and 1D.

Generation of a detectable signal can be achieved in a number of ways. In one method, a large number of reporter groups which generate a detectable signal, are attached directly to the secondary probes prior to their use. There is no interference with subsequent attachment of the secondary probes to the primary probe because the methods used do not incorporate the signaling reporter groups in the region of the secondary probe which binds to the primary probe. In a second method, an intermediate substrate is attached to the secondary probes. The substrate may, for example, be an immunogenic protein, to which antibody molecules can bind, each containing any of a variety of reporter groups. Alternatively, the substrate may be capable of binding the reporter groups through a coupling system. A third method incorporates the ability to modify the secondary probe in such a way that the probe itself becomes the reporter group; in other words the secondary probe itself generates the detectable signal.

The hybridization assay of the present invention may be performed in a number of ways but each method involves the following steps which may be performed simultaneously or in a series of steps:

(a) contacting the target sequence with the primary probe under conditions which allow hybridization to occur;

(b) contacting the family of secondary probes with the hybridization reaction products formed in step (a) above under conditions which permit binding of the secondary probes to the tail of the primary probe; and (c) detecting the signal generated by the seconary probes which are bound in the hybridization complex.

In practice, the target nucleic acid sequences may first be immobilized on a variety of solid supports; alternatively a liquid system could be used. Each system has its own peculiar characteristics, and must be chosen with consideration for the type of signal generated. Each system is amenable to automation.

The probes and method of the invention can be used for the detection of polynucleotides in the research and clinical laboratory, as well as in food, agricultural and veterinary sciences. It is a very powerful diagnostic device for the determination of pathogenic organisms (bacteria, viruses, fungi, yeast, protozoa) in human and veterinary medicine, and for the determination and detection of cancerous cells and genetic defects in chromosomes.

The present invention is directed to the hybridization assays, production of an amplification system based upon nucleic acid hybridization, and methods for the attachment of reporter groups to hybridization probe molecules. It is estimated that an enormous amplification will result for the detection of target nucleic acid sequences.

For the purposes of clarity, the description of the invention has been divided into the following categories: (a) description of primary and secondary probes; (b) description of reporter groups; and (c) use and automation of the hybridization probe systems of the present invention.

5.1. PRIMARY PROBES

As previously explained, the primary probe comprises a single-stranded polynucleotide sequence which is complementary to the target sequence and which is attached to a polymeric tail that does not bind to the target sequence. The probe must form a stable hybridization with the target sequence. It is generally understood that at least about 10 to 12 contiguous basepair interactions define a stable hybridization.

The portion of the primary probe which is complementary to the target sequence may comprise either DNA or RNA and must be single stranded before use to allow for hybridization to the target sequence. It usually, but need not be, produced by cloning the target sequence into a recombinant vector such as a plasmid or virus which can be used to generate many copies of the sequence. Alternatively, the primary probes may be synthesized by chemical methods. These procedures are well known to one skilled in the art.

Only the complement to the target sequence need be nucleic acid. The remainder of the primary probe i.e., the tail can consist of any polymer, natural or synthetic, which can be coupled to the nucleotide sequence and to which reporter groups can be bound or to which secondary probes can be reacted. Examples include, but are not limited to, polymers of nylon, plastics, cellulose fiber, rayon, cotton fiber, polysaccharides, nitrocellulose, etc. In this case the secondary probes comprise the same or a different polymer, a portion of which binds to the tail of the primary probe.

A particularly useful embodiment is obtained when the primary probe comprises a substantially single-stranded polynucleotide, and the secondary probes comprise a family of polynucleotides each containing a single-stranded portion which hybridizes to different segments of the primary probe tail. When both primary probe including its tail comprise polynucleotides, the entire probe can be relatively easily generated through recombinant DNA techniques. Accordingly, the primary probe may be cloned using a recombinant vector such as plasmid or viral DNA. In fact, the primary probe may comprise the entire length of a recombinant vector molecule which contains the target sequence.

Vector systems which provide a particular advantage for the cloning and production of single stranded primary probes comprise vectors derived from the filamentous bacteriophages such as M13 and f1. These phage vectors are capable of producing large quantities of easily purified single stranded DNA molecules in complementary orientations. In fact, opposite phage DNA orientations are packaged separately in the f1 phage system, thus enabling the purification and isolation of either the plus or minus strand for use as a primary probe. The primary probe may be constructed using these phage vectors by inserting the target gene sequence into a cloning site of the vector. Secondary probes can be prepared using similar vectors containing sequences that hybridize to the "tail" portions of the primary probe, i.e., regions of the primary probe vector outside the cloning sites. Alternatively, in addition to the target sequence, other foreign DNA sequences may be cloned into the primary probe vectors in the "tail" portion of the probe in order to incorporate unique sequences to which secondary probes can be made to hybridize.

The resulting recombinant molecules which can readily be isolated as single-stranded nucleotide probes can be used as circular probes or can be converted to linear molecules by a number of methods. In particular, an oligonucleotide which encodes a restriction enzyme recognition site that is unique to the vector may be allowed to hybridize to the circular single-stranded vector. Subsequent digestion with the restriction enzyme results in linearization of the probe molecule. Alternatively, linearization can be achieved using certain restriction enzymes which can cut single-stranded DNAs at their recognition sequences at a slow rate (e.g., HindIII). Alternatively, circular probes can be non-specifically linearized, for example, by nicking the the strands with ultraviolet light or incubating at 100° C. for several minutes.

Another advantage obtained using vector systems as a supply of primary probes is that a primary probe cassette can be constructed. The cassette comprises a vector with (a) a multiple cloning site that enables the insertion and cloning of any target DNA and (b) a second portion(s) of the vector which is complementary to and capable of binding secondary probes i.e., the "tail" portion of the primary probe. These cassettes can be used to prepare primary probes containing any desired target sequence to be used in conjunction with the same family of secondary probes. The family of secondary probes adds a powerful new dimension to hybridization technology, namely, the ability to use the same set of secondary probes for the detection of any target gene, regardless of sequence and source. The insertion of any target gene DNA sequence into the primary probe cassette, followed by production of primary probes, results in the maintenance of the invariant secondary probe recognition sequence. Consequently, the user need only construct a single primary probe containing the target sequence. This primary probe may be used in conjunction with the same family of secondary probes that contain a readout system in order to obtain an amplified signal.

In another embodiment, RNA synthesis reactions may be used to generate primary and secondary probes. For example, sequences corresponding to primary or secondary probes may be cloned into the SP6 or T7 phage promoters. RNA transcripts are generated which may incorporate reporter groups as, for example, radioactive groups or modified nucleotides capable of generating a detectable signal as described earlier.

5.2. SECONDARY PROBES

As previously explained, the secondary probes comprise a family of signal-generating probes each of which comprises a signal-generating component and a segment capable of binding to a portion of the tail of the primary probe. The composition of the secondary probe is dependent upon the composition of the primary probe tail. For instance, where the primary probe tail comprises a non-nucleic acid polymer such as natural or synthetic polymers, the secondary probe may comprise the same or a different polymer, a portion of which binds to the tail of the primary probe.

Where the tail of the primary probe comprises a polynucleotide that is essentially single-stranded the secondary probes can comprise a family of polynucleotides each containing a single-stranded portion which hybridizes to different segments of the tail of the primary probe; the signal-generating component of this family of secondary probes may comprise single- or double-stranded polynucleotides which have been modified so that the nucleotides themselves generate a signal or so that attached reporter groups generate a signal.

The secondary probes which comprise polynucleotides may be produced using recombinant DNA techniques or chemical synthetic methods. A convenient method for producing the polynucleotide secondary probes by recombinant DNA techniques involves cloning the probe nucleotide sequence using, for example, the same methods discussed for cloning the primary probes; the secondary probes however, will lack the target sequence. At least two general approaches may be taken to prepare the secondary probes: (a) a single-stranded cloning vector which does not hybridize to the tail of the primary probe can be modified by the insertion of specific sequences that are complementary to portions of the tail of the primary probe; or (b) a single-stranded cloning vector which is complementary to the tail of the primary probe can be modified so that all but a specific portion is no longer able to form base-pairs.

In one embodiment of the invention, polynucleotide secondary probes can readily be constructed using recombinant DNA techniques by selecting a cloning vehicle which will not hybridize to the primary probe. For example, such vehicles may include vectors which differ in nucleotide sequence from that of the primary probe or vectors which have a sequence identical to, and therefore, non-complementary to that of the primary probe. Nucleotide sequences which are complementary to a portion or portions of the tail of the primary probe can be inserted into an appropriate cloning site and cloned into these vectors so that a recombinant molecule is constructed in which only a segment of the molecule is capable of hybridizing to the tail of the primary probe. The inserted sequences may be the complement of sequence which naturally occur in the tail portion of the primary probe or of foreign sequences which were cloned into the tail portion of the primary probe. The resulting secondary probes (e.g., the recombinant ssDNA vectors) will be capable of hybridizing to particular portions of the primary probe tail due to the inserted complementary nucleotide sequences. The remainder of the cloning vehicle, however, will not hybridize to the primary probe tail and, therefore, may be utilized as the signal generating component of the secondary probes by modification or attachment of reporter groups. The signal generating component can be conferred on these molecules by nonspecific labeling at subsaturating condition or by protection/deprotection reactions, which involve protecting the region that hybridizes to the primary probe tail, altering the unprotected regions of the molecule so that reporter groups are acquired or conferred on the molecule and deprotecting the secondary probes. Accordingly, a family of signal-generating secondary probes, each containing a cloned sequence that is complementary to a different portion of the primary probe tail may be constructed. Vector systems which provide a particular advantage for the cloning and production of single-stranded secondary probes comprise vectors derived from the filamentous bacteriophages such as M13 and f1. The circular single-stranded probes which result may be linearized if desired, as previously described for primary probes.

This embodiment of the invention is described more fully and demonstrated in the examples infra, in which pEMBL+ or M13 primary probe was constructed to contain an SV40 target DNA sequence and a foreign sequence, namely Tn5. Five secondary probes containing different portions of this Tn5 sequence were cloned in the complementary orientation in M13. Hybridization of these primary probes to their family of secondary probes resulted in the formation of complexes in which the five secondary probes hybridized to different regions of the tail of the primary probe, which in turn hybridized to the test target SV40 DNA sequence. Detection of the complexes was achieved by the incorporation of reporter groups into the family of five secondary probes. This system served to amplify the initial hybridization event between the primary probe and the SV40 test target DNA sequence. The secondary probes, when devoid of the complementary Tn5 DNA elements were incapable of hybridizing to the primary probe.

In another embodiment of the invention, a single-stranded cloning vector which is complementary to the tail of the primary probe can be modified so that all but a specific portion is no longer able to form base-pairs. The filamentous bacteriophage vectors can be used to produce the single-stranded primary probes in one orientation, and these same vectors can also be used to produce the family of secondary single-stranded probes in the opposite orientation. Thus the bacteriophages can be used to produce primary probes in the "+" (sense orientation) which contain the sequence complementary to the target sequence, and a family of secondary probes in the "−" (antisense) orientation that are complementary to the primary probe, and vice versa. Once these single-stranded secondary probes are produced, the probes are modified so that only a different segment of each secondary probe is able to hybridize to a different portion of the primary probe tail, thus, creating the family of molecules. This may be accomplished by (a) protecting a short region at a different location on each secondary probe; (b) altering the molecules so that the unprotected region of each molecule acquires a reporter group or is itself converted to a reporter group and is thereafter unable to hybridize; and (c) deprotecting the secondary probe. The product is a family of secondary probes each of which contains a segment capable of binding to a different portion of the tail of the primary probe, while the remainder of the molecule, which cannot bind to the tail of the primary probe, generates a detectable signal.

Protection of the secondary probe is easily accomplished by the hybridization of a short single-stranded complementary polynucleotide. After alteration of the unprotected regions to confer the signal generating component, the molecule is deprotected most easily by denaturation and separation of the short protective polynucleotide. Where the secondary probes are circular molecules they can be deprotected by denaturation or by nuclease digestion using exonucleases which only digest linear polynucleotides.

The particular embodiment below describes such a method for the production of primary and secondary probes using the filamentous bacteriophage f1 plasmid. The primary probe is defined in this embodiment as the pSP64f+ orientation ssDNA which also contains the target gene sequence. The target gene sequence is inserted into the polylinker region of the plasmid by standard cloning techniques and plasmids are propagated in E. coli strains JM101 or NM522. Large quantities of ssDNA molecules containing the target sequence can be produced using a published procedure (Dente et al., 1983, Nuc. Acids. Res. 11: 1645–1655). The resulting primary probe, which contains the target sequence (e.g., any gene of interest such as an SV40 DNA sequence, an homologous Herpesvirus or human DNA segment and the like) is produced in the (+) (i.e., sense) strand orientation.

Production of ssDNA secondary probes is achieved using pSP64f(−) using the same methods described for the (+) orientation; however, no target gene is inserted into the vector. In order to generate a family of secondary probes, the pSP64f(−) ssDNAs are divided into at least 5 samples. To each sample, hybridize a short ssDNA fragment (from about 20 to 500 bases) corresponding to a different region, creating a population of 5 ssDNA circles, each protected in a different region. The short ssDNA molecules which are added have been previously produced either by restriction enzyme digests of plasmids followed by purification of ssDNA molecules from strand separation gels, or by synthesis of oligonucleotides. The unprotected single-stranded DNA regions are available for modification by a variety of techniques, all of which utilize the secondary probe strand as a substrate to bind reporter groups. These are described more fully in Section 5.3. After modification of the unprotected regions to form the signal generating component, the secondary probes may be linearized if desired, and the protected region deprotected in either of two ways:

(a) Denaturation and nicking: Denature at 100° C., nick circles with a titrated amount of DNase I required to produce 1 hit per circle. Separate the small DNA fragment from the large secondary probe based upon size difference (e.g. column chromatography). Alternatively, a restriction enzyme can be used to cut at a single site at the end of a duplex followed by denaturation and separation.

(b) Enzymatic digestion of protected regions: Either lambda phage exonuclease or E. coli exonuclease III may be used to digest the linear DNA fragment using standard reaction conditions. The ssDNA circles may be linearized as described above using DNaseI.

Regardless of the method chosen to prepare secondary probes, the family of secondary probes constructed need not be re-engineered even when used to detect a new and different target. Only the primary probe containing the new target sequence need be constructed. This may be accomplished easily by inserting the new target sequence into the primary probe cassette and cloning the primary probe. The same family of secondary probes can be used in conjunction with the new primary probe.

Furthermore, the secondary probe need be single stranded only in the region to be hybridized to the primary probe. In a particularly useful embodiment, DNA synthesis reactions can be used to generate detectable primary and seconday probes. Nick translation of the secondary probe DNAs devoid of the primary probe recognition sequence can be used to generate labeled segments capable of hybridizing to the entire family of secondary probes. These segments can provide the detectable signal by incorporation of radioactive nucleotides, or modified nucleotides (such as BuDR modified nucleotides which can be identified by antibodies against BuDR) which can serve as reporter groups. Alternatively, second strand synthesis reactions using a short "primer" segment can be used to incorporate modified or radiolabeled nucleotides into a second strand complementary to part of the secondary probe which does not interfere with its ability to hybridize to the tail of the primary probe.

In yet another embodiment secondary RNA probes may be prepared using methods previously explained for primary probes.

5.3. REPORTER GROUPS

Several embodiments of the present invention are outlined below whereby reporter groups are generated on the secondary probes for the purpose of detection and quantitation of target nucleic acid sequences. The nature of the reporter groups and respective modifications to produce reporter groups is determined, to some extent, by the composition of the secondary probes.

5.3.1. CONVERSION OF SECONDARY PROBES TO REPORTER GROUPS

Chemically modified secondary nucleic acid probe themselves can function as a reporter group. Modifications include, for example, the incorporation into nucleotides of radioisotopes, biotin (to be used in conjunction with avidin-coupled reporter molecules), and sugar (to be used in conjunction with lectin coupled reporters). A particularly attractive modification is the conversion of the secondary ssDNA or ssRNA probe to a fluorescent nucleic acid derivative. This is achieved by treatment of the protected secondary probes with chloroacetaldehyde, at slightly acidic conditions, which converts non-base paired adenine (and to a lesser extent cytosine residues) to fluorescent etheno-derivatives.

Typical reaction conditions consist of incubating the protected secondary probes at from 100 to 500 ug/ml in 2M chloracetaldehyde, 20 mM potassium acetate pH 4.5 for 10 to 24 hours at 37° C. Unreacted chloracetaldehyde is generally removed by dialysis or column chromatography. Reacted probe may be concentrated by ethanol precipitation. Usually, 70% to 100% of un-paired (i.e., non-basepaired) adenine-residues (A-residues) are modified to become fluorescent etheno-derivatives. The chemical will only modify ssDNA, so the secondary probe region which was chosen to hybridize to the primary probe will be protected by hybridization with a complementary sequence which will later be removed. Modification of ssDNA has the added advantage of completely eliminating hybridization of un-protected regions. An additional amplification of the fluorescence signal can be achieved by the digestion of hybridization complexes which form as a product of the assay with nucleases that release free nucleotides, resulting in a concomitant large increase in fluorescent intensity.

5.3.2. ATTACHMENT OF REPORTER GROUPS TO SECONDARY PROBES

A variety of reporter groups can be attached to secondary probe by several means. These groups can be attached to the probes directly or indirectly. Reporter groups that can be used include, but are not limited to: (a) a variety of enzymes which perform detectable functions (e.g. alkaline phosphatase, horse-radish peroxidase), (b) electron dense or electrical groups detectable by electron microscopy or electrical properties such as conductivity (e.g. ferritin or colloidal gold), (c) chromophores (e.g., fluorescent compounds, dyes), (d) radioactive molecules (e.g. $^{32}P$, $^{125}I$), and (e) chemically reactive molecules (e.g. compounds that can be induced to undergo or cause a color change).

The method used to directly attach the reporter group to the probes will vary depending upon the nature of the composition of the probe and the reporter groups. Either covalent or non-covalent linkages can be used. Where the secondary probes comprise nucleotides, various reactive sites can be generated on the probe molecule including but not limited to amino groups, phospho groups, hydroxyl groups, etc., which can be used as sites for attachment of the reporter molecules.

Reporter groups can be indirectly attached to the signal generating component of the secondary probes by a number of methods. These involve the attachment of reporter groups to the secondary probe via another agent. A number of approaches are possible including but not limited to the following: (a) the agent can be a bifunctional linker which serves as a link between the secondary probe and the reporter group; (b) the agent can be a substrate for the reporter group (e.g. where the reporter group is an enzyme the agent attached to the secondary probe can be the substrate for the enzyme); (c) the agent can be the antigen which is specific for an antibody molecule labeled with the reporter group; and (d) the agent can be a chemical group such as biotin to which an avidin-linked reporter molecule can conjugate or vice versa. Such agents can also include, but are not limited to, agarose beads, latex particles, dextran bead, controlled pore glass and silica, nitrocellulose, cellulose fibers and paper, rayon, saccharide moieties, nylon and other synthetic polymers, and crystals (e.g. piezocrystals). To all of these reporter groups can be coupled. The substrates themselve can be used for detection, for example, by detectable derivitization reactions.

In particular embodiments where the secondary probes comprise nucleotides, many proteins are available which can be used to attach reporter molecules. In fact, one could take advantage of the natural affinity of certain proteins for particular kinds of nucleotides; for example, E. coli SSB, fd phage SSB and bacteriophage T4 gene 32 protein each binds specifically to ssDNA molecules; histones and a number of polymerases bind specifically to dsDNA molecules; eucaryotic mRNP particles bind specifically to ssRNA molecules; and some eucaryotic translation initiation factors specifically bind to dsRNA molecules. Alternatively these or other proteins can be covalently bound to the secondary probe regardless of their natural affinity for the probe.

A particularly useful reaction called photoconjugation, which involves a photo-activated alkylation, can be used to conjugate protein and other molecules to the secondary probes which were detected using a enzyme-linked avidin colorimetric reaction. Indeed, photobiotinylation was used in the examples infra to covalently attach biotin to secondary probes which were detected using an enzyme-linked avidin colorimetric reaction. Similarly, fluorescent reporter groups may also be conjugated to nucleic acids by a similar reaction to that of photobiotinylation. Detection of fluoresceinated probes may then be achieved by directly recording the resulting fluorescence upon excitation with ultraviolet light. Alternatively, antibody molecules directed against the fluorescein group may be used to carry in reporter groups such as alkaline phosphatase.

In another embodiment E. coli SSB may be purified as described (Schneider and Wetmur, 1982 Biochem. 21, 608–615) and added to protected secondary probes to achieve 100% saturation of unprotected (single-stranded) regions. Alternatively, SSB may be added at sub-saturating levels (e.g., 50 to 70% to unprotected secondary probes. Typical binding conditions for complete saturation consist of 20–200 ug/ml secondary probe, 8:1 (w/w) SSB to secondary probe in 150 mM NaCl, 10 mM TrisHCl, pH8, 1 mM EDTA at room temperature for 30 minutes. SSB is cross-linked to itself and ssDNA as follows: protein-protein crosslinking is performed by making the solution 0.1% in glutaraldehyde with gentle stirring for 1 hour. Glutardaldehyde is removed by dialysis. Protein-ssDNA crosslinking is performed by irradiating the mixture with short wave UV light, according to standard procedures. Signals may be generated, for example, by the addition of anti-SSB antibodies conjugated to a variety of reporter groups or by directly incorporating these reporter groups into SSB itself.

Another attractive signal generating system consists of binding multiple copies of the enzyme beta-galactosidase to the secondary probes. Enzyme can be coupled, for example, directly to probes, or coupled to antibodies directed against probe bound substrates. Hybridization can be quantitated by the subsequent addition of the non-fluorescent substrate fluoroscein di (beta-D-galactopyranoside), which is cleaved by beta-glactosidase to generate a fluorescent derivative, fluoroscein (Rotman, 1961, Proc. Natl. Acad. Sci. USA, 47, 1981–1991).

5.4. THE HYBRIDIZATION ASSAY

The hybridization assay of the present invention can be accomplished in a number of ways, however each method involves the following steps which may be performed simultaneously, in series or in reverse order of that indicated below:

(a) contacting the target sequence with the primary probe under conditions which allow hybridization to occur between complementary sequences;

(b) contacting the family of secondary probes with the hybridization reaction products formed in step (a) above under conditions that permit binding of secondary probes to the tail of the primary probe; and (c) detecting the signal generated by the secondary probes which are bound in the hybridization complex. Hybridization results in formation of the following physical complex: the primary probe is bound to the target nucleic acid, and multiple copies of secondary probes are bound to primary probes (See FIG. 1).

The assay may be conducted by immobilizing the target sequence on a variety of solid supports including but not limited to nitrocellulose, agarose beads, modified cellulose fibers, polypropylene, or sephacryl, and the like. The targe sequence could be immobilized via noncovalent interactions with the solid support. Alternatively, the target sequence could be covalently attached to solid supports using methods known in the art so that the target sequence is immobilized but remains capable of hybridization (Albarella et al., EPO 144914 A2; Dattagupta and Crothers EPO 130523 A2; Yabusalu et al., WO 85/02628). Alternatively, an amplified sandwich hybridization assay may be accomplished in which the target DNA is allowed to anneal to an immobilized sequence that does not interfere with binding of the primary probe, and the immobilized target is contacted with the primary probe and family of secondary probes of the invention.

As a result of these methods, the hybridization complexes will be immobilized and the signal generated by the reporter groups can be detected on the solid support. Alternatively, after the immobilized hybridization complexes have been formed, and the unreacted components separated or removed from the system, the hybridization complex can be disrupted so that the signal is released and generated in the liquid phase of the assay system. In either configuration the signal generated may be read and quantified.

In yet another embodiment of the invention, hybridization reactions can be accomplished using mobile components in solution. The hybridization complexes which form in solution can then be immobilized using an "anchor sequence" i.e., a sequence which is immobilized or which can readily be immobilized and which can hybridize to a portion of the target sequence that does not interfere with binding of the primary probe. For example, the hybridization complexes formed in solution can be immobilized using a biotinylated anchor sequence and an avidin-coated solid support. According to this embodiment, the hybridization reactions could be accomplished in solution and the hybridization complexes could be immobilized in avidin-coated microtiter wells. A similar separation technique has very recently been demonstrated using a conventional hybridization assay (see Syvanen et al., 1986, Nucleic Acids Research 14(12): 5037–5048) and, therefore, could be adapted by the skilled artisan in the practice of the present invention.

5.5. AUTOMATION OF HYBRIDIZATION ASSAY

The present invention can be made to be fully automated. The type of detection system utilized depends upon the signal generated by the reporter groups. Detection systems can include, but are not limited to, automated observation of fluorescence, color changes and electrical conductivity.

Detection can be accomplished using a variety of systems, each of which has its own advantages for different methods of rapid processing. For example, the signal generated from immobilized hybridization complexes of the present invention can be detected directly from the solid support. Alternatively, the hybridization complexes can be released from the solid support in which case the signal may be detected in solution. In addition, the entire hybridization assay can be performed free in solution, i.e., liquid hybridization. If reaction products are subsequently immobilized, for example in microtiter wells, the signal generated can readily be read and quantified.

In an example of one such system, target nucleic acids can be fixed to solid supports in capillary tubes. Hybridization reactions can be performed in capillary tubes by an automatic process in which probes are delivered mechanically. Detection of signals such as fluorescence and color changes can be performed using a high intensity light source and fiber optics for observation. Electrical conductivity can be determined by measuring the resistance of the solution or the electron flow in, for example, a piezo-electric crystal.

6. EXAMPLE: CONSTRUCTION OF PRIMARY AND SECONDARY PROBES FOR USE IN AMPLIFIED HYBRIDIZATION ASSAYS

The construction of a primary probe cassette and its family of secondary probes used in the examples herein are described below. The primary probe cassette contains (a) a multiple cloning site into which any desired target DNA sequence can be inserted and (b) a Tn5 DNA sequence. The packaged (+) single-strands of the cassettes contain the antisense Tn5(−) DNA to which the family of secondary probes containing Tn5(+) DNA can hybridize.

6.1 MATERIALS AND METHODS

Tn5 DNA was obtained from plasmid pEG81, a PBR322 plasmid which contains a full-length Tn5 insertion near the PvuII site (Lupski et al., 1984, Gene 30: 99-106). The bacteriophage f1 vector pEMBL8+ (Dente et al., 1983, Nucl. Acids Res. 11: 1645-1655), and bacteriophage M13 vector mp10 were propagated in *E. coli* TG-1, a DH-1 (rec A-) variant. pEMBL8+ plasmids were mobilized into single-stranded DNA (ssDNA) forms using the Ir1 bacteriophage (Dente et al., 1983, Nucl. Acids Res. 11: 1645-1655). Plasmid DNAs were purified by the clear lysate method and purified on CsCl gradients (Humphreys et al., 1975, BBA 383: 457-463). Bacteriophage ssDNAs were purified by PEG/NaCl precipitation and phenol:-chloroform extraction as described by Dente et al., supra, 1983. Uniformly labeled phage vector ssDNAs were prepared according to Gaynor et al., 1982, (J. Vir. 44, 276-285) using 1mCi $^{32}PO_4$ per 15 ml culture. DNAs contained between 1 to $3 \times 10^5$ cpm/ug.

DNA restriction fragments were analyzed and extracted from agarose gels using standard techniques (Maniatis, et al., 1982, Molecular Cloning, A Laboratory Manual, Cold Spring Harbor, pp. 150-164). DNA ligations, transformations and analysis of transformants were as described in Maniatis et al., 1982, supra, pp. 286-291, pp. 250-252 and pp. 368-369. Restriction endonucleases and other DNA modifying enzymes were from Boehringer Mannheim, and used as suggested by the supplier. Bacteria were grown in LB or M9 media (Maniatis et al., 1982, supra, pp. 60-73).

6.2 CONSTRUCTION OF PRIMARY PROBE CASSETTES

The initial prototype of the primary probe cassette was constructed in a bacteriophage f1 pEMBL8+ vector (Dente et al., 1983, Nucl. Acids Res. 11, 1645-1655). A Tn5 DNA fragment was inserted into the vector to introduce a hybridization target for secondary probe DNAs (described below). Tn5 was selected because it has been demonstrated to be stably carried in the related fd bacteriophage (Auerswald et al., 981, CSHQB, 45: 107-113).

Figure 2:
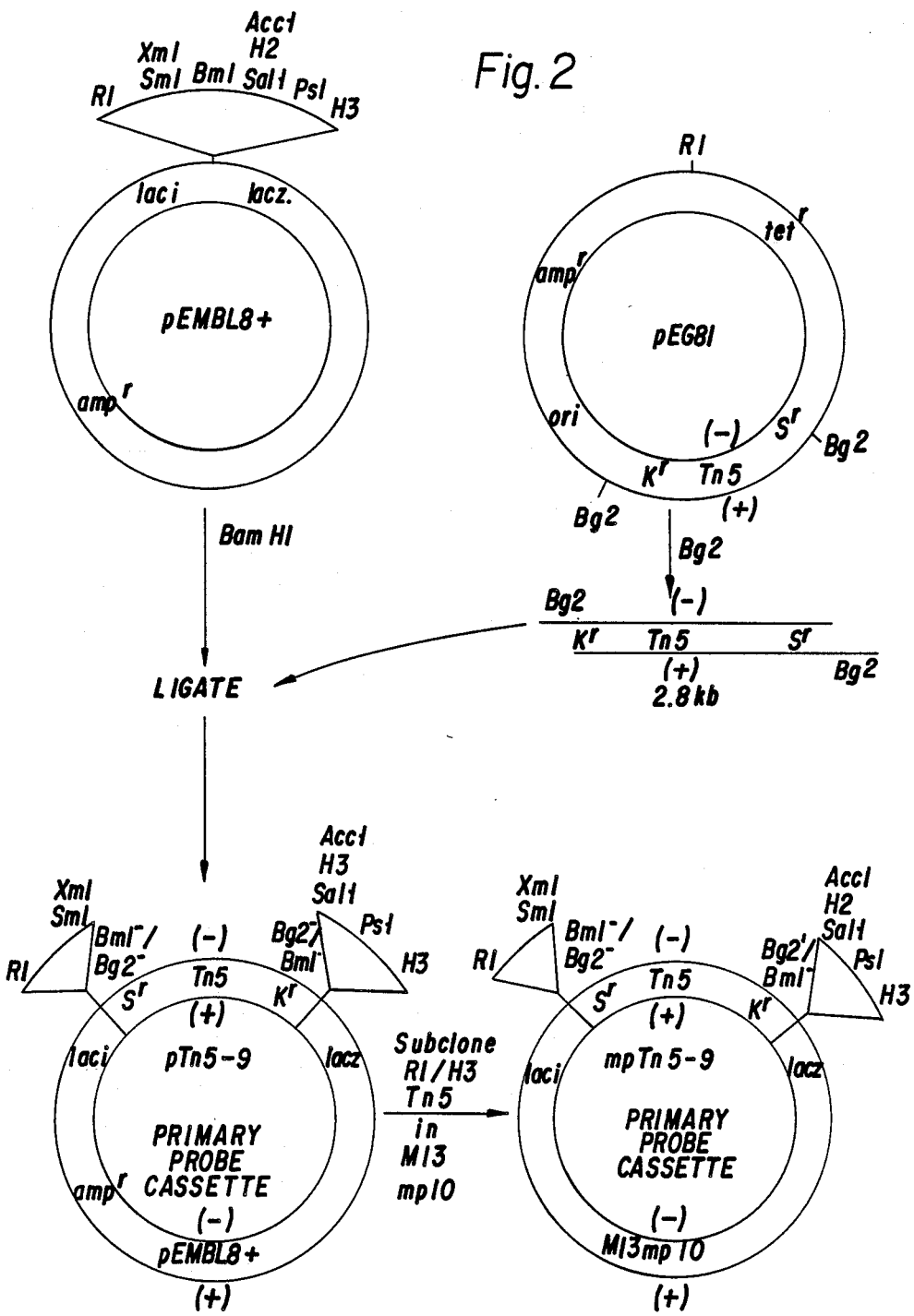
FIG. 2 is a representation of the construction of two primary probe cassettes pTN5-9 and mpTn5-9 as explained in detail in Section 7.2 infra. The packaged (+) single-strands of these cassettes contain the antisense Tn5(−) sequence which is complementary to the sense Tn5(+) sequences contained in the secondary probes depicted in FIG. 3.

The primary probe cassette was constructed by inserting a Tn5 2.8 kbp BglII DNA fragment into pEMBL8+ at the BamHI site (see FIG. 2). This Tn5 fragment contains the coding region for the kanamycin and streptomycin drug resistance gene. Positive transformants were then chosen, and those with the fragment in the orientation shown in FIG. 2 were screened by further restriction fragment analysis to identify pTn5-9. This orientation positions the Tn5 kanamycin gene next to the pEMBL8+ lacZ gene. Production of (+) sense ssDNA circles contained a 2.8 kbp Tn5(−) DNA fragment to which the family of secondary probes containing Tn5(+) sequences can bind. By convention, (+) is defined as the sense identical to the mRNA coding strand. The primary probe cassette pTn5-9 still has polylinker sites for EcoRI, SmaI, SalI, PstI, and HindIII which flank the Tn5 DNA as shown in FIG. 2. These multiple cloning sites can be used to insert any target DNA sequence into the primary probe cassette.

An M13 variant of pTN5-9 was constructed by subcloning the EcoRI/HindIII Tn5 fragment into M13mp10, to construct mpTn5-9 (see FIG. 2). As a result of this construction the Tn5 DNA replaces the polylinker of M13mp10.

6.3 CONSTRUCTION OF SECONDARY PROBES

Figure 3:
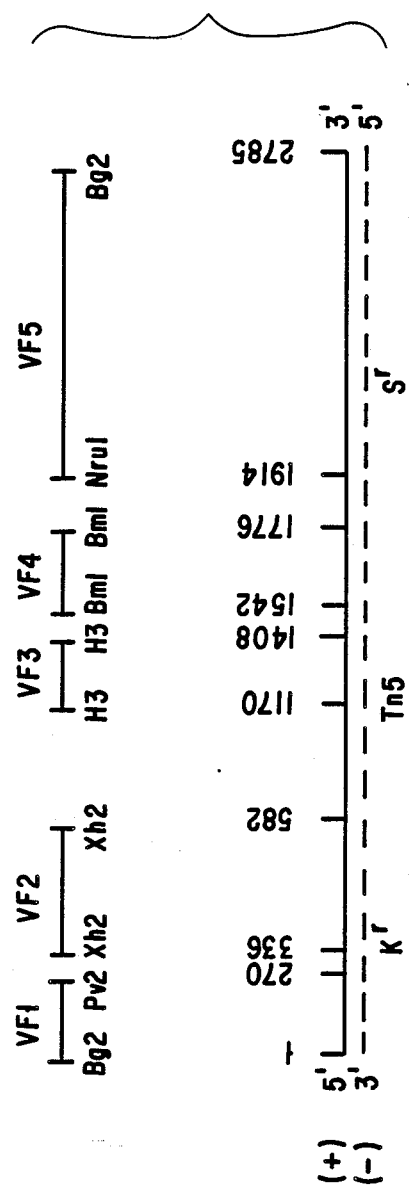
FIG. 3 represents the five segments of the Tn5(+) sequence which are contained in the family of secondary probes which can be used in conjunction with primary probes prepared from the cassettes in FIG. 2. The regions indicated as VF1, VF2, and VF4 were each cloned into PEMBL8+ and all five regions were cloned into M13mp10 (see Section 7.3 infra).

Five secondary probes were constructed, some in pEMBL8+, and all in M13mp10 vectors. Each packaged recombinant ssDNA contains a different segment of the Tn5(+) 2.8 kbp fragment, but inserted in the opposite orientation (antisense) to the full length Tn5(−) sequence contained in the ssDNA primary probe cassette. The Tn5(+) specific DNA inserts in the secondary probes range from 234 to 871 bps (FIG. 3). The construction of each secondary probe is described below:

Secondary Probes pVF1 and mpVF1: A 270 bp Tn5 BglII/PvuII fragment (nucleotides 1 to 270 of the BglII Tn5 fragment) was inserted into pEMBL8+ at the BamHI/HindII sites to construct pVF1. The M13 variant, mpVF1, was constructed by subcloning the EcoRI/HindIII Tn5 containing fragment from pVF1 into M13mp10.

Secondary Probes pVF2 and mpVF2: A 246 bp Tn5 XhoII fragment (nucleotides 336 to 582 of the BglII Tn5 fragment) was inserted into pEMBL8+ at the BamHI site. Positive transformants with the fragment in the "anti-sense" direction were chosen by further restriction enzyme analysis for proper orientation, to create pVF2. The M13 variant, mpVF2, was constructed by subcloning the Tn5 fragment into M13mp10.

Secondary Probe mpVF3: A 238 bp Tn5 HindII fragment (nucleotides 1170 to 1408 of the BglII Tn5 fragment) was inserted into M13mp10 at the HindII site. Positive transformants were screened for the "antisense" orientation by further restriction enzyme digests and mpVF3 was identified.

Secondary Probes pVF4 and mpVF4: A 234 bp Tn5 BamHi/BalI fragment (nucleotides 1542 to 1776 of the BglII Tn5 fragment) was inserted into pEMBL8+ at the BamHi/HindII sites to construct pVF4. The M13 variant, mpVF4, was also constructed by subcloning the EcoRI/HindIII fragment into M13mp10.

Secondary Probe mpVF5: An 871 bp Tn5 NruI/BglII fragment (nucleotides 1914 to 2785 of the BglII Tn5 fragment) was inserted into M13mp10 at the SmaI/BamHI sites to construct mpVF5.

7. EXAMPLE: DETECTION OF TARGET DNA USING AN AMPLIFIED RADIOLABELED HYBRIDIZATION ASSAY

The use of the primary probe cassette and the secondary probes constructed in Section 6 to detect SV40 target DNA sequences is demonstrated in the subsections below. To this end, SV40 target DNA was cloned into the multiple cloning site of the primary probe cassette in order to construct the primary probe specific for SV40 target sequences. Hybridization was detected via radioactive reporter groups which were incorporated into the secondary probes. The data disclosed in the subsections below demonstrate that the amplified signal generated using the assay of the invention allows for the detection of small amounts of target SV40 DNA sequences.

7.1. MATERIALS AND METHODS

7.1.1. INSERTION OF THE TARGET SEQUENCE INTO THE PRIMARY PROBE CASSETTE

An SV40 sequence was used as a test target DNA. In order to construct primary probes containing an SV40 target, a 525 bp HindIII DNA fragment from the SV40 early region T-antigen gene (nucleotides 3476 to 4002 of the SV40 map) was inserted into the HindIII site of the pTN5-9 or mpTN5-9 cassettes to construct the primary probes, pTn5-94 or mpTn5-94, respectively (see FIG. 4A). The single-stranded primary probes containing the SV40 DNA and the Tn5(−) DNA insert were purified as described in Section 6.1.

7.1.2. RADIOACTIVE LABELING OF SECONDARY PROBES

Secondary probes constructed in Section 6.3 were labeled in vivo using $^{32}PO_4$ (50–1000 Ci/mM, New England Nuclear, MA), and the single-stranded secondary probes containing the Tn5(+) DNA inserts were purified as described in Section 6.1.

7.1.3 HYBRIDIZATION PROCEDURE

Nitrocellulose filters (Schleicher and Schuell) were presoaked in 10xSSC and fitted to a Schleicher and Schuell minifold dot-blot apparatus. Single-stranded DNA samples were applied in 25 ul volumes containing 10xSSC and 50 ng carrier salmon sperm ssDNA, and washed extensively with 10xSSC. Filters were baked at 80° C. under vacuum for 1–2 hours. Preparation of blots was essentially as described by Thomas (1980, Proc. Natl. Acad. Sci. U.S.A., 77: 5201–5205). Blots were prehybridized from 4 hours to overnight in 50 mM Tris-HCl, pH 7.5, 0.5% SDS, 1 mM EDTA, 3×SSC, 1× Denhardt's solution, 1 mg/ml salmon sperm ssDNA (and where indicated, 50% formamide), at 43° C. (for formamide) or 68° C. (aqueous). Hybridizations were carried out overnight, as above, but with 100 ug/ml salmon sperm DNA. Except where noted, filters were washed as follows: 2×5 minutes in 2xSSC, 0.5% SDS (sodium dodecyl sulfate) at 25° C.; 60 minutes at 68° C. in 0.1xSSC, 0.5% SDS; 20 minutes at 68° C. in 0.1xSSC, 0.5% SDS. Radioactive spots were detected by autoradiography at −70° C. using Kodak XAR-5 film and intensifying screens.

7.2. DETECTION OF TARGET DNA

The demonstration that secondary probe DNAs can successfully detect a primary probe hybridized to a target DNA sequence was performed in dot-blot experiments utilizing linear probes. To this end, all probe DNAs (labeled and unlabeled) were linearized (see FIG. 4). To linearize the single-stranded primary probe, a single-stranded oligonucleotide 12 residues long which was complementary to the phage vector polylinker PstI site (i.e., complementary to 5'-GACCTGCAGCCA-3') was synthesized using an applied Biosystems Synthesizer. The synthetic oligonucleotides were annealed to the circular primary probe ssDNAs at a 10:1 molar ratio, in order to create a double stranded PstI recognition site which was then digested with the restriction enzyme PstI. This site was chosen because it separates the Tn5(−) and SV40 DNA elements of the primary probe to opposite ends of the linearized molecule. To linearize the five radio-labeled secondary probes, a similar scheme was employed using an oligonucleotide complementary to the EcoRI site (see FIG. 4A).

SV40 target DNA was digested with HindIII, denatured, and applied to nitrocellulose filters. From 100 ng to 100 pg were applied in the presence of 50 ng salmon sperm ssDNA carrier. After prehybridization, one blot was hydrized with about 200 ng/ml labeled primary probe (about $1.2 \times 10^5$ cpm); see FIG. 5A. Another blot was first hybridized with about 100 ng/ml unlabeled primary probe followed by 200 ng/ml labeled secondary probes (about $1.5 \times 10^6$ cpm); see FIGS. 4B and 5B. The amount of labeled primary probe was one-tenth, rather than one-fifth, of the five combined secondary probes. Nevertheless, FIG. 5 clearly demonstrates the amplification system of the invention. These results indicate that hybridization with the family of labeled secondary probes is about 5-fold to 25-fold more sensitive than the labeled primary probe alone (compare the 1.0 ng and 0.1 ng SV40 DNA spots in FIGS. 5A and 5B). This demonstrates that an unlabeled primary probe hybridized to the target SV40 DNA sequence, and was in turn bound by up to five labeled secondary probes (see FIG. 4B which depicts the hybridization complexed diagrammatically).

8. EXAMPLE: ULTRASTRUCTURAL ANALYSIS OF THE HYBRIDIZATION COMPLEXES

The hybridization complexes which formed between primary probe cassettes and secondary DNA probes were visualized by electron microscopy.

All DNA probes consisted of the purified, ssDNA molecules prepared in Section 6. The secondary probes were linearized by incubation for 5 minutes at 100° C., which introduces about one nick per molecule. The primary probe was maintained as a single-stranded circle to aid in identification of authentic hybridization complexes. Only three of the five secondary probes were used in the hybridization assay in order to facilitate clear visualization of the complexes. Approximately 20 ng of the circular primary probe and 20 ng of each linear secondary probe were hybridized for 4 hours in 50% formamide and 5xSSC at 43° C. before an aliquot was removed for electron microscopic visualization.

After hybridization, DNA samples were spread on a hypophase according to Davis et al. (1971, Methods Enz. 21: 413–428), picked up on parlodian covered copper grids (3%) and subjected to tungsten-platinum rotary shadowing at about an eight-degree angle using a Penton vacuum electron beam gun. DNAs were visualized in a Zeiss electron microscope and photographs taken. Original magnification on negatives varied from 6300 to 40,000.

In the hybridization complexes observed, three linear secondary probes were clearly seen bound to one circular primary probe in the hybridization complex. Careful examination of the complex indicated that all three secondary probes were hybridized to a region of the primary probe that encompasses about $\frac{1}{3}$ to $\frac{1}{2}$ of the circle. This is to be expected only if hybridization specifically occurs between the primary probe Tn5(−) DNA element (which represents about 40% of the DNA circle), and the complementary Tn5(+) elements in the secondary probes.

9. EXAMPLE: DEMONSTRATION OF HYBRIDIZATION COMPLEXES USING NON-RADIOACTIVE LABELS

The data in the subsections below demonstrate the detection of hybridization complexes using non-radioactive reporter groups. To demonstrate that secondary probe DNAs can successfully detect a primary probe using a non-radioactive reporter group, we employed the well studied avidin-biotin system (Langer et al., 1981, PNAS 78: 6633-6637). This system takes advantage of the extremely high binding constant between avidin and biotin (Green, 1975, Adv. Prot. Chem. 29: 85-133), allowing minute quantities of biotin to be detected when avidin coupled reporter groups are used. To this end, secondary probes were biotinylated as described below and used with primary probe cassettes in a dot blot format. Hybridization of biotinylated secondary probes to the primary probe cassettes was detected using an avidin-linked enzymatic colorimetric assay in a dot blot format.

9.1. MATERIALS AND METHODS: PHOTOBIOTINYLATION AND COLOR DEVELOPMENT

Photocrosslinking of photobiotin acetate to single-stranded probe DNAs performed as suggested by the suppliers (Bresa Ltd. Australia; and Forster et al., 1985, Nucl. Acids Res. 13: 745-761), using a 450 watt mercury discharge lamp (Philips MLR 500w), for various times. The single-stranded secondary DNA probes were reacted with photobiotin acetate, a photo-activatable analogue of biotin which will derivatize ssDNA after irradiation with visible light (Forster et al., 1985, Nucl. Acids Res. 13: 745-761). Since photobiotin can be used to label only about 1% of the nucleotides in DNA (higher levels leads to precipitation and decreased hybridization), the degree of modification was determined by varying reaction times. It was found that a 5 to 15 minute irradiation produced optimal crosslinking density. These reaction conditions were used in this study.

Color development was performed using avidin-alkaline phosphatase (Bresa Ltd. Australia). Filters were blocked and color development carried out according to the manufacturer's instructions. After color development, filters were fixed and stored in 10 mM Tris HCl pH8, 1 mM EDTA.

9.2. DETECTION OF HYBRIDIZATION COMPLEXES

To demonstrate hybridization of probe complexes, decreasing amounts of single-stranded primary probe cassettes (constructed in Section 6) were applied to nitrocellulose filters. The primary probe cassettes were prepared from unmodified, primary probe cassette dsDNA plasmids (pTn5-9) which were first digested with EcoRI and denatured before use, although the phage vector ssDNA worked just as well. Ten-fold serial dilutions were used, ranging from 50 ng to 5 pg. About 15 ng of each circular biotinylated secondary probe (i.e., pVF1, pVF2, mpVF3, pVF4 and mpVF5) was hybridized to the primary probe cassettes using aqueous conditions (68° C., overnight). Blots were washed as previously described, except the high temperature wash was reduced to 37° C. The hybridization of secondary probes to the primary probe cassettes was detected using avidin-linked alkaline phosphatase and a colorimetric assay (nitroblue tetrazolium). Color development was terminated after a 4 hour incubation.

The results of this experiment are shown in FIG. 6. Lane 1 contains decreasing amounts of control, biotinylated M13 ssDNA which served as a standard. The M13 DNA is modified to a level of about 1-2%. Secondary probe DNAs used in the assay were photo-biotinylated for either five minutes (lane 2) or 15 minutes (lane 3).

After only 4 hours of color development, hybridization complexes could be clearly detected down to the 500 to 50 pg range. In fact, hybridization complexes can be seen even in the 5 pg range, but not as clearly. It is important to point out, however, that these experiments were not designed to determine the maximum sensitivity of the system. Much greater sensitivity can certainly be achieved by increasing the concentration of modified secondary probes as well as the development time. Very small quantities of modified secondary probe DNAs were used, and color development was terminated after only 4 hours. These results do demonstrate, however, that small quantities of primary probe DNA are easily detected by modified secondary probes using a non-radioactive readout system. By comparison to the M13 DNA standard, these results also indicate that approximately 5% of the input secondary probe DNAs actually bound to the primary probe. This is certainly within the expected efficiency range for solid phase hybridization.

9.3. AMPLIFICATION OF SIGNAL

To further demonstrate the amplification achieved using the method of the invention, a dot blot hybridization experiment was performed in which the primary probe cassette was detected using one, two, three, four or all five biotinylated secondary probes. In this experiment, 100 ng spots of single-stranded primary probe cassette pTn5-9 were applied to nitrocellulose filters as previously described. Individual filters were then hybridized with from one to five biotinylated secondary probes (50 ng of each). Filters were washed and color development performed as before. Colorization reactions were terminated after 4 hours. The filters were scanned with a densitometer in order to assess the level of amplification achieved. Results are presented in Table I below. Absorbance plots were automatically integrated to provide the relative peak areas for each experimental point in Table I.

TABLE I

| AMPLIFICATION OF SIGNAL GENERATED IN THE HYBRIDIZATION ASSAY | | |
|---|---|---|
| Number of Secondary Probes | Peak Area* | Amplification Factor** |
| 1 | 0.14 | 1.0 |
| 2 | 0.14 | 1.0 |
| 3 | 0.37 | 2.6 |
| 4 | 0.52 | 3.7 |
| 5 | 0.86 | 6.1 |

*Densitometric scan of blue spots using LKB Ultrascan XL.
**Ratio of peak area in comparison to peak area generated by 1 probe.

The results in Table I demonstrate that the amplification of the signal generated is directly related to the number of secondary probes used in the assay system.

The present invention is not to be limited in scope by the examples disclosed since these embodiments are intended as illustrations of various aspects of the invention and any embodiment which is functionally equivalent is within the scope of this invention. Indeed, various modifications of the invention in addition to those shown and described herein will become apparent to those skilled in the art from the foregoing description and accompanying drawings. Such modifications are intended to fall within the scope of the appended claims.

It should also be noted that all references to kbp and bp are approximate.

What is claimed is:

1. A method for the detection of a target nucleotide sequence, comprising:
   (a) contacting the target nucleotide under conditions that permit hybridization with (i) a primary probe which comprises a polynucleotide sequence that is complementary to the target nucleotide sequence and a polymeric tail that has binding sites that are incapable of binding to the target sequence, and (ii) a plurality of secondary probes comprising a family of signal-generating probes each member of which comprises a signal generating component and a polymer capable of binding to a different portion of the tail of the primary probe; and
   (b) detecting the amplified signal generated by a reaction product formed in step (a), in which the polynucleotide sequence of the primary probe is hybridized to the target nucleotide and a plurality of secondary probes are bound to different portions of the primary probe tail.

2. The method according to claim 1 in which the tail of the primary probe comprises a synthetic polymer.

3. The method according to claim 1 in which the tail of the primary probe comprises a natural polymer.

4. The method according to claim 1 in which the tail of the primary probe comprises a single-stranded nucleotide polymer.

5. The method according to claim 4 in which the nucleotide polymer comprises deoxyribonucleic acid.

6. The method according to claim 4 in which the nucleotide polymer comprises ribonucleic acid.

7. The method according to claim 1 in which the secondary probe comprises a synthetic polymer.

8. The method according to claim 1 in which the secondary probe comprises a natural polymer.

9. The method according to claim 1 in which the secondary probe comprises a nucleotide polymer.

10. The method according to claim 9 in which the secondary probe comprises deoxyribonucleic acid.

11. The method according to claim 9 in which the secondary probe comprises ribonucleic acid.

12. The method according to claim 1 in which the signal generating component of the secondary probe comprises a chromophore.

13. The method according to claim 1 in which the signal generating component of the secondary probe comprises a radioactive compound.

14. The method according to claim 1 in which the signal generating component of the secondary probe comprises an enzyme-substrate system that generates a detectable product.

15. The method according to claim 14 in which the enzyme comprises beta-galactosidase.

16. The method according to claim 14 in which the enzyme comprises alkaline phosphatase.

17. The method according to claim 1 in which the signal generating component of the secondary probe comprises a fluorescent compound.

18. The method according to claim 17 in which the fluorescent compound comprises an etheno-derivative of a single-stranded nucleic acid molecule.

19. The method according to claim 1 in which the signal generating component comprises a reporter group indirectly attached to the secondary probe via an agent.

20. The method according to claim 19 in which the reporter group is attached to avidin and the secondary probe is biotinylated.

21. The method according to claim 19 in which the secondary probe comprises a single-stranded nucleic acid molecule and the agent comprises a single-strand binding protein.

22. The method according to claim 1 in which the tail of the primary probe comprises a heteropolynucleotide.

23. The method according to claim 1 in which the secondary probe comprises a signal-generating heteropolynucleotide.

24. The method according to claim 12, 13, 14, 17 or 20 in which the secondary probe comprises a signal-generating heteropolynucleotide.

25. A hybridization assay kit for the detection of a target nucleotide sequence, comprising:
   (a) a primary probe which comprises a polynucleotide sequence that is complementary to the target nucleotide sequence and a polymeric tail that has binding sites that are incapable of binding to the target sequence; and
   (b) a plurality of secondary probes comprising a family of signal-generating probes each member of which comprises a signal-generating component and a polymer capable of binding to a different portion of the tail of the primary probe, which provides for the generation of an amplified signal when the polynucleotide sequence of the primary probe is hybridized to the target nucleotide and the plurality of secondary probes are bound to different portions of the primary probe tail.

26. The kit according to claim 25 in which the tail of the primary probe comprises a single-stranded nucleotide polymer.

27. The kit according to claim 26 in which the nucleotide polymer comprises ribonucleic acid.

28. The kit according to claim 26 in which the nucleotide polymer comprises deoxyribonucleic acid.

29. The kit according to claim 25 in which the secondary probe comprises a natural polymer.

30. The kit according to claim 25 in which the secondary probe comprises a nucleotide polymer.

31. The kit according to claim 30 in which the secondary probe comprises deoxyribonucleic acid.

32. The kit according to claim 30 in which the secondary probe comprises ribonucleic acid.

33. The kit according to claim 25 in which the signal generating component of the secondary probe comprises a chromophore.

34. The kit according to claim 25 in which the signal generating component of the secondary probe comprises a radioactive compound.

35. The kit according to claim 25 in which the signal generating component of the secondary probe comprises an enzyme-substrate system that generates a detectable product.

36. The kit according to claim 35 in which the enzyme comprises beta-galactosidase.

37. The kit according to claim 35 in which the enzyme comprises alkaline phosphatase.

38. The kit according to claim 25 in which the signal generating compound of the secondary probe comprises a fluorescent compound.

39. The kit according to claim 38 in which the fluorescent compound comprises an etheno-derivative of a single-stranded nucleic acid molecule.

40. The kit according to claim 25 in which the signal generating component comprises a reporter group indirectly attached to the secondary probe via an agent.

41. The kit according to claim 40 in which the reporter group is attached to avidin and the secondary probe is biotinylated.

42. The kit according to claim 40 in which the secondary probe comprises a single-stranded nucleic acid molecule and the agent comprises single-strand binding protein.

43. The kit according to claim 25 in which the tail of the primary probe comprises a natural polymer.

44. The kit according to claim 25 in which the tail of the primary probe comprises a synthetic polymer.

45. The kit according to claim 25 in which the secondary probe comprises a synthetic polymer.

46. The hybridization assay kit according to claim 25 in which the tail of the primary probe comprises a heteropolynucleotide.

47. The hybridization assay kit according to claim 25 in which the secondary probe comprises a signal-generating heteropolynucleotide.

48. The hybridization assay kit according to claim 33, 34, 35, 38 or 41 in which the secondary probe comprises a signal-generating heteropolynucleotide.

49. A hybridization assay kit for the detection of a target nucleotide sequence, comprising:
  (a) a primary probe cassette which comprises a cloning vector having (i) a multiple cloning site into which a target nucleotide sequence can be inserted and cloned and (ii) nucleotide sequences which are capable of hybridizing to their complements which comprise a plurality of secondary probes; and
  (b) the plurality of secondary probes comprising a family of signal-generating probes each member of which comprises a signal-generating component and a nucleotide sequence capable of hybridizing to a different portion of the portion of the primary probe described in (a)(ii), which provides for the generation of an amplified signal when the plurality of secondary probes are hybridized to different portions of the portion of the primary probe described in (a)(ii).

50. The hybridization assay kit according to claim 49 in which the tail of the primary probe comprises a heteropolynucleotide.

51. The kit according to claim 49 in which the signal generating component comprises a reporter group indirectly attached to the secondary probe via an agent.

52. The kit according to claim 51 in which the reporter group is attached to avidin and the secondary probe is biotinylated.

53. The kit according to claim 51 in which the secondary probe comprises a single-stranded nucleic acid molecule and the agent comprises single-strand binding protein.

54. The hybridization assay kit according to claim 49 in which the secondary probe comprises a signal-generating heteropolynucleotide.

55. The kit according to claim 49 in which the signal generating component of the secondary probe comprises a chromophore.

56. A kit according to claim 49 in which the signal generating component of the secondary probe comprises a radioactive compound.

57. The kit according to claim 49 in which the signal generating compound of the secondary probe comprises a fluorescent compound.

58. The kit according to claim 57 in which the fluorescent compound comprises an etheno-derivative of a single-stranded nucleic acid molecule.

59. The kit according to claim 49 in which the signal generating component of the secondary probe comprises an enzyme-substrate system that generates a detectable product.

60. The kit according to claim 59 in which the enzyme comprises beta-galactosidase.

61. The method according to claim 59 in which the enzyme comprises alkaline phosphatase.

62. The hybridization assay kit according to claim 55, 56, 59, 57 or 52 in which the secondary probe comprises a signal-generating heteropolynucleotide.

* * * * *